United States Patent [19]
Golz et al.

[11] Patent Number: 5,716,599
[45] Date of Patent: Feb. 10, 1998

[54] COSMETIC KAOLIN-CONTAINING PREPARATION

[75] Inventors: Karin Golz; Leonhard Zastrow, both of Monaco, Monaco; Klaus Stanzl, White Plains, N.Y.; Alfred Braunagel, Mainz, Germany

[73] Assignee: Lancaster Group GmbH, Ludwigshafen, Germany

[21] Appl. No.: 836,435

[22] PCT Filed: Dec. 6, 1995

[86] PCT No.: PCT/DE95/01801

§ 371 Date: May 9, 1997

§ 102(e) Date: May 9, 1997

[87] PCT Pub. No.: WO96/17588

PCT Pub. Date: Jun. 13, 1996

[30] Foreign Application Priority Data

Dec. 7, 1994 [DE] Germany ............... 44 45 064.8

[51] Int. Cl.$^6$ ...................................................... A61K 7/00
[52] U.S. Cl. ................................................ 424/47; 514/951
[58] Field of Search ................................ 514/951; 424/47

[56] References Cited

U.S. PATENT DOCUMENTS 5,182,103  1/1993  Nakane et al. .................. 424/78.03

*Primary Examiner*—Amelia Averill Owens
*Attorney, Agent, or Firm*—Collard & Roe, P.C.

[57] ABSTRACT

The invention involves a cosmetic preparation containing kaolin which may be employed as a mask, lotion, gel or cream with a non-sticky, non-plasticized consistency and with a content of white kaolin with a high proportion of kaolinite and spherical inorganic particles of a particle size of less than 5 μm, with a proportion of spherical particles in the kaolin mixture of 0.5 to 10% by weight as well as a cosmetic skin care composition, in which the proportion of the kaolin/spherical particle mixture falls within the range of over 2 to 65% by weight of the composition as a whole. The viscosity of the composition with the proportion of kaolin/spherical particles is around 2000 to over 15,000 cps higher than a similar composition with kaolin only and without spherical particles, with the difference in viscosity increasing with the proportion of kaolin/spherical particles.

The new, pleasantly soft preparation with an inhibitive effect with regard to inflammation permits high kaolin contents to be used to especially good effect in masks and gels.

8 Claims, No Drawings

COSMETIC KAOLIN-CONTAINING PREPARATION

This application is a 371 of PCT/DE95/01801 filed Dec. 6, 1995 published as WO96/17588 Jun. 13, 1996.

The invention pertains to new preparations containing kaolin which may be employed in cosmetics in the form of emulsions or gels.

It is known that inflammation may be inhibited to a degree through the addition of kaolin to certain dermatological preparations. Previously, kaolin additives of up to 2% by weight were possible while maintaining a consistently pleasant sensation on the skin; the emulsion tended to clot severely above this limit. The addition of a greater proportion also led to the dulling of the emulsion, an effect that cannot be tolerated in cosmetics.

Substrates in platelet form of a certain size, e.g. of zeolite, mica or glass, containing a proportion of spherical particles for the prevention of agglomeration are known from EP-B-406657. A composite powder coated with aluminum metasilicate which may also contain kaolin and which has improved adsorption properties is known from U.S. Pat. No. 5,182,103.

The objective of this invention is the development of new cosmetic preparations which, in addition to their skin care effects, provide an increased inhibitive effect with regard to inflammation as well as providing a particularly pleasant sensation on the skin.

According to the invention, the cosmetic preparation containing kaolin consists of (a) a mixture of white kaolin with a high degree of kaolinite, preferably over 85% by weight, in particular over 95% by weight, modified with spherical inorganic particles with a particle size of less than 5 µm in a proportion of 0.5 to 10 by weight of the kaolin mixture and (b) a cosmetic skin care composition of the emulsion and emulsion base group for lotions, creams and masks; gels and gel bases for lotions, creams and masks in which the proportion of the kaolin/spherical particle mixture, based on the overall composition, is in the range of over 2 to 65% by weight; and in which the viscosity of the overall composition including the proportion of kaolin/spherical particles remain under that of the same composition with kaolin but without spherical particles by 2000 to over 15,000 cps and in which the difference in viscosity increases with the proportion of kaolin/spherical particles.

A further characteristic of the invention is that the cosmetic preparations mentioned above provide a particularly pleasant sensation on the skin and have a non-sticky, non-plasticized consistency.

Kaolin mixtures with a proportion of spherical particles of 0.5 to 5% by weight are particularly favorable. In addition, it is advantageous if the size of the spherical particles is in the range of 0.1 to 3 µm, especially in the range of 0.1 to 1 µm.

The proportion of modified kaolin mixture (kaolin/spherical particles) is usable in the entire range from approx. 2 to approx. 65% by weight; it is particularly favorable if the proportion of the modified kaolin mixture lies in the range from 5 to 30% by weight, although still higher proportions are possible, especially in powders.

Surprisingly, not only can an improvement of the agglomeration within the kaolin suspension be achieved through the formulation of a kaolin mixture with a low proportion of spherical inorganic particles such as amorphous silicon dioxide, but the introduction of kaolin in cosmetic compositions such as emulsions becomes possible in such high proportions as would not have been expected by a specialist. The employed kaolin, with a platelet diameter in the range of 0.2 to 1 µm, does not form a superordinate macrostructure with the roughly equally-sized $SiO_2$ particles, thus avoiding the known condition of plasticity of clays and resulting in a lower viscous dispersion as opposed to the usual mixtures of kaolin and aqueous cosmetic additives, which lead to mixtures with signs of plasticity.

A further synergistic effect is the hitherto unachieved sensation of softness of the complete preparation on the skin; the cosmetic effect of comparable products is surpassed and a significant inhibitive effect with regard to inflammation is simultaneously achieved.

An additional surprising effect may be observed with gels, in that the addition of modified kaolin to a gel mixture of only 2.5 to 3% strongly reduces its stickiness and significantly improves the spreading characteristics of certain gels. The scope of application of gels in cosmetics is thus widened.

The viscosity of the cosmetic formulations according to the invention, e.g. as a cosmetic mask, is around 2000 cps lower with a proportion of 2.5% by weight of the kaolin/spherical particle mixture as opposed to the same mixture without the spherical particles; at 30% by weight, about 15,000 cps lower and at 45% by weight significantly more than 15,000 cps lower. The measurements were performed with a Brookfield RVT/DVII viscometer with the C, D, E and F hydrometers. With the F hydrometer, the viscosity of the mixture with pure kaolin without spherical particles at 45% by weight was over 65,000 cps and no longer measurable, whereas with the kaolin/spherical particle mixture (45% by weight), it amounted to about 52,000 cps.

It may be advantageous for compositions according to the invention to be contained in conventional liposomes or—more favorably—in asymmetric lamellar aggregates, in which these aggregates consist of phospholipids and oxygen-charged fluorocarbon or fluorocarbon mixture with a fluorocarbon content in the range of 0.2 to 100% by weight/volume, the phospholipids have a phosphatidylcholine content of over 30 to 99% by weight and in which the skin penetration of these aggregates is dependent upon the critical solubility temperature of fluorocarbons.

In addition, the aggregates may also be present in the cosmetic preparation charged with oxygen only.

These aggregates are oxygen carriers and permit the penetration of oxygen into the skin, thus improving the oxygen supply of the skin. The production of these aggregates is accomplished by the high-pressure homogenization of phospholipids such as soya lecithin or egg lecithin, synthetic phospholipids or partially hydrogenated phospholipids with a phosphatidylcholine content of over 30 to 99% by weight with perfluorinated or highly fluorinated carbon compounds or mixtures thereof which are able to transport gasses such as oxygen or carbon dioxide. In addition to phosphatidylcholine, lysolecithins in the concentration range from 0.1 to 10% by weight and/or electrically-charged phospholipids such as phosphatidylethanolamine, N-acetylphosphatidylethanolamine or phosphatidic acid in the concentration range from 0.1 to 30% by weight may be present.

Unlike the known aqueous liposomes (vesicles), these phospholipid-stabilized aggregates carry hydrophobic fluorocarbons capable of transporting oxygen in their core. Their boundary-layer stabilization is accomplished primarily through a monolayer with an inverse arrangement, to which a structure of bilayer films is optionally attached. Because of this peculiarity of their structural arrangement, these novel aggregates are designated as asymmetrical lamellar oxygen carriers. Their unusual colloid chemical stability may be traced back to the lamellar structure and the surface charge of the aggregates. The latter can be traced back to the choice of suitable phospholipids or mixtures thereof of natural as well as of synthetic origin. Phospholipids, especially phosphatidylcholine in the specified concentration range from 30 to 99% in connection with lysolecithins in the concentration from 0.1 to 10% and/or charged phospholipids in the concentration range from 0.1 to 30% by weight are primarily responsible for the favorable action in this sense. The claimed action of the phospholipids is verified by appropriate negative zeta potentials and by the measurement of charge densities (on titration with a cationic polyelectrolyte). The skin penetration in dependence of the critical solubility temperature of the selected fluorocarbons or fluorocarbon mixtures is essential for the employment of the fluorocarbon aggregates (for the employment of asymmetrical lamellar aggregates, also refer to DE-B-42 21 255).

The proportion of the aggregates charged with the modified kaolin mixture may be in the range of 5 to 60% by weight of the complete preparation and are favorably located in the range of 10 to 50% by weight, especially in the range of 15 to 30% by weight.

As described earlier, common liposomes may also be used as a transport system for the modified kaolin mixture in the preparations according to the invention. Liposomes are completely closed bilayer lipid membranes containing an aqueous volume. Liposomes may be unilamellar (with a single-membrane bilayer) or multilamellar vesicles (onion-like structures characterized by a multi-membrane bilayer, with each separated from the next by an aqueous layer). The bilayer consists of two lipid monolayers with a hydrophobic "tail" section and a hydrophile "head" section. The structure of the membrane bilayer is such that the hydrophobic (non-polar) "tails" of the lipid monolayer orient themselves toward the center of the bilayer, while the hydrophile "heads" orient themselves toward the aqueous phase.

The production of liposomes using saturated and unsaturated lipids has been described in many patents, as well as their application as a transport system. The introduction of the modified kaolin mixture may be performed in the usual manner.

Preparations containing kaolin and the products of cautious ultrasonic maceration and/or high-pressure homogenization of suspensions or dispersions of vegetable cells, bacteria or yeasts are preferable according to the invention. Vegetable substances which have been previously used to good advantage in cosmetics, such as chamomile, aloe vera, etc. may be employed, as well as products such as the bark of the Mexican skin tree, *Mimosa tenuiflora*, which results in a particularly anti-inflammatory, oxygen-rich product.

Baker's, brewer's, wine yeast or other yeast types may be employed.

A particularly advantageous maceration product results from the use of an ultrasonication flow-through cell in accordance with DE 42 41 154, in which the synotrode projects by ½ to ⅔ of its length into the flow-through cell, the angle of the synotrode in the acoustic irradiation vessel is within the range from 80.5° to 88.5°, in that the ratio of the extent of immersion of the synotrode (in mm) to the acoustic irradiation volume (in ml) is set to a value within the range from 1:1.1 to 1:20 and in that the ratio of the extent of immersion of the synotrode (in mm) to the proportion of solid matter in the medium to be sonicated (in percent by weight) is within the range from 1:0.02 to 1:2.2.

The effect of the favored combination of asymmetric lamellar aggregates, charged with the modified kaolin mixture and the maceration products of vegetable and yeast cells in a cosmetic preparation according to the invention is especially pronounced in the maceration of superoxide dismutase-rich yeast which deliver a high content of superoxide dismutase (SOD). As SOD is effective as a trap of radicals in the skin and catalyses the reaction

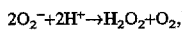

it is, per se, an especially favorable component in cosmetic or dermatological preparations. However, other radical traps may be used which are suited to the bonding of free oxygen radicals, such as vitamin E.

Suitable forms of cosmetic preparation are emulsions, preferably cosmetic masks, especially facial masks. For such masks, the content of modified kaolin suspension is advantageous in the range from 3 to 30% by weight, preferably 5 to 20% by weight. In addition, the emulsion may contain the usual components, such as emulsifiers, perfume oils, protective substances and other skin care components.

Gels are favored as well due to their already-mentioned spreading characteristics; in this case the proportion of the modified kaolin preferably should lie in the range from 5 to 15% by weight.

The kaolin/spherical particle mixture may also be employed in powders as well as pharmaceutical preparations.

The production of the preparation is generally implemented by the mixture of a dispersion of purified white kaolin with a high proportion of kaolinite with a dispersion of spherical inorganic particles at ambient temperature. Water is the preferable dispersing agent. The preparation is then mixed with the cosmetic skin care composition, insofar as this is available as an emulsion, in an emulsification machine.

After the mixture of the kaolin dispersion with the spherical particle dispersion, especially a $SiO_2$ dispersion, the product may be spray-dried and the dried product directly processed into the emulsion or absorbed in liposomes or asymmetrical lamellar aggregates and then processed into the emulsion.

In the following, the invention shall be described in detail by examples. All percent figures are by weight.

EXAMPLE 1

Production of Modified Kaolin (1)

30 l of a suspension of 4 kg of white kaolin with a kaolinite content of 96% in water/ethyl alcohol is stirred and added to 40 l of a dispersion of 4.5 kg monodisperse silicon dioxide over the course of half an hour and stirred for a further hour. The product is then spray-dried in a conventional spray tower. The result is a product which is suitable for direct processing in cosmetic products.

EXAMPLE 2

Production of Modified Kaolin (2)

The process is as in example 1, with the exception that a multivalent alcohol such as ethylene glycol is used as a solvent and 3.5 kg of kaolin are used.

EXAMPLE 3

Cosmetic Mask (1)

5 separate phases are produced which are consecutively mixed, partly under intensive homogenization. The phases A to D are processed at an elevated temperature (40° to 70° C.) and phase D processed at the end at ambient temperature.

| Phase A | |
|---|---|
| glyceryl stearate | 4.1% |
| stearic acid | 1.8% |
| cetyl alcohol | 1.8% |
| Phase B | |
| distilled water | q.s. |
| carbomer | 0.3% |
| propylene glycol | 2.5% |
| preservative | 0.3% |
| Phase C | |
| triethanolamine (TEA) | 0.3% |
| Phase D | |
| modified kaolin | 30% |
| chamomile active agent complex | 3% |
| Phase E | |
| perfume oil | 0.5% |

EXAMPLE 4

Cosmetic Gel

The carbomer is homogenized with water; TEA, preservative and the modified kaolin are consecutively added while stirring.

| | |
|---|---|
| carbomer | 1.0% |
| TEA | 0.8% |
| water | q.s. |
| modified kaolin | 2.5% |
| preservative | 0.3% |

EXAMPLE 5

Cosmetic Powder

The ingredients listed below are mixed in the order indicated.

| | |
|---|---|
| modified kaolin | 65% |
| magnesium stearate | 5% |
| silk protein | 10% |
| zinc oxide | 5% |
| maize/rice protein | 10% |
| color | approx. 5% |

EXAMPLE 6

Kaolin-Charged Liposomes

Liposomes charged with modified kaolin (in accordance with examples 1 and 2) were produced as follows. A phospholipid is introduced into a water-kaolin suspension, in which the kaolin was produced in accordance with example 2. After thorough homogenization, ethyl alcohol is stirred in and homogenized further.

| | |
|---|---|
| phospholipid | 15% |
| modified kaolin | 7% |
| water | q.s |

EXAMPLE 7

Kaolin-Charged Aggregates

Asymmetric lamellar aggregates charged with modified kaolin (in accordance with examples 1 and 2) were produced as follows. Modified kaolin is introduced to perfluorodecaline mixed with glycerin and propylene glycol and thoroughly homogenized. A phospholipid with a phosphatidylcholine content of 50% is stirred into this homogenized mixture and water added. After thorough homogenization, the aggregates charged with modified kaolin are ready for further use.

| | |
|---|---|
| phospholipid | 25% |
| modified kaolin | 4% |
| fluorocarbon (perfluorodecaline) | 50% |
| glycerin | 3.5% |
| propylene glycol | 5.0% |
| water | q.s. |

EXAMPLE 8

This is produced as in example 7, with the exception that the proportion of modified kaolin amounted to 10%.

EXAMPLE 9

This is produced as in example 7, with the exception that in addition to the modified kaolin, macerated bakery yeast in the form of the supernatant centrifugate produced by the ultrasonification process described above is homogenized into the fluorocarbon mixture.

| | |
|---|---|
| phospholipid | 20% |
| modified kaolin | 5% |
| glycerin | 3.5% |
| propylene glycol | 5% |
| yeast maceration | 16% |
| perfluorodecaline | 40% |

EXAMPLE 10

This is produced as in example 9, with the exception that a 19.5% proportion of the maceration product of the bark of the Mexican skin tree (*Mimosa tenuiflora*) is added.

EXAMPLE 11

Sunscreen

After the homogenization of phases A and B at an elevated temperature, these are mixed with one another and homogenized thoroughly. Phase C is then mixed in at about 30° to 40° C.

| Phase A | |
|---|---|
| sorbitan sesquioleate | 5.0% |
| cetyl alcohol | 4.5% |
| stearyl alcohol | 3.5% |
| titanium dioxide | 3.6% |
| Phase B | |
| propylene glycol | 2.0% |
| water | q.s. |
| glycerin | 1.0% |
| titanium dioxide | 1.9% |
| Phase C | |
| preservative | 0.3% |
| perfume oil | 0.4% |
| asymmetrical lamellar aggregates charged with modified kaolin as per example 9 | 30.0% |

EXAMPLES 12 and 13

After Sun Gel

The asymmetrical lamellar aggregates produced as in examples 9 and 10 and charged with modified kaolin and a yeast or Mexican skin tree (*Mimosa tenuiflora*) maceration, as well as perfume oil and preservative are consecutively stirred into the complete gel at ambient temperature.

| | |
|---|---|
| polyacrylic acid (molecular weight approx. 4,000,000) | 1.0% |
| hydroxyethyl cellulose | 0.3% |
| propylene glycol | 3.0% |
| benzoic acid | 0.3% |
| modified kaolin with yeast/ *Mimosa tenuiflora* maceration in aggregates | 25.0% |
| perfume oil | 0.3% |
| preservative | 0.3% |
| water | q.s. |

EXAMPLE 14

Cosmetic Mask (2)

This is produced as in example 3, with the exception that the quantity of modified kaolin amounted to 12%.

EXAMPLE 15

Pharmaceutical Ointment

After homogenization and homogenous blending of the phases A and B at an elevated temperature (approx. 65° C.), phase C is added at 30° to 40° C.

| | |
|---|---|
| Phase A | |
| lanolin | 5.0% |
| cetyl alcohol | 2.0% |
| cetyl alcohol and PEG-40 castor oil, 1:1 | 3.0% |
| hexyl laurate | 1.5% |
| Phase B | |
| water | q.s. |
| glycerin | 2.0% |
| propyl alcohol | 2.0% |
| modified kaolin | 45% |
| Phase C | |
| preservative | 0.3% |

Comparative Example 1

A cosmetic neck-décolleté mask was applied to ten female test persons. Mask A corresponded to the example 14 in accordance with the invention. Mask B contained normal kaolin with a kaolinite content of 97%, in which the kaolin content had to be reduced to 8% as a result of processing difficulties. The evaluation by the test persons was performed on the basis of the following scale:
1=very pleasant skin sensation;
2=pleasant skin sensation;
3=unpleasant skin sensation;
4=very unpleasant skin sensation.

| | Evaluation in Percent | | | |
|---|---|---|---|---|
| | 1 | 2 | 3 | 4 |
| Mask A | 90 | 10 | 0 | 0 |
| Mask B | 0 | 0 | 80 | 20 |

The clear superiority of the mask in accordance with the invention with regard to the sensation on the skin may thus be recognized. A comparison with regard to anti-inflammatory effectiveness could not be made due to the varying kaolin contents.

We claim:

1. Cosmetic preparation containing kaolin, characterized by its availability as a lotion, mask, cream or gel with a particularly pleasant sensation on the skin and a non-sticky, non-plasticized consistency, consisting of a mixture of white kaolin with a high proportion of kaolinite and spherical inorganic particles of silicon dioxide or titanium dioxide with a particle size of less than 5 μm and a proportion of spherical particles in the kaolin mixture of 0.5 to 10% by weight, dispersed in an aqueous cosmetic preparation of the emulsion and emulsion base group for lotions, creams and masks as well as gels and gel bases for lotions, creams and masks;

the proportion of the kaolin/spherical particle mixture falls within the range of over 2 to maximally 65% by weight of the composition as a whole;

the viscosity of the composition with the share of kaolin/spherical particles is at least 2,000 cps, preferably 2,000 to 15,000 cps lower than the same composition with kaolin only and without spherical particles, with the difference in viscosity increasing with the proportion of kaolin/spherical particles.

2. Cosmetic preparation containing kaolin according to claim 1, characterized by the proportion of spherical particles of 0.5 to 5% by weight of the kaolin mixture.

3. Cosmetic preparation containing kaolin according to claim 1, characterized by the size of the spherical particles which lies in the range of 0.1 to 3 μm, particularly in the range of 0.1 to 1 μm.

4. Cosmetic preparation containing kaolin according to claim 1, characterized by the proportion of the kaolin/spherical particle mixture which amounts to 5 to 30% by weight.

5. Cosmetic preparation containing kaolin according to claim 1, characterized by the containment of the kaolin/spherical particle mixture in asymmetric lamellar aggregates consisting of phospholipids and oxygen-charged fluorocarbon or fluorocarbon mixture in which the proportion of fluorocarbon lies in the range from 0.2 to 100% by weight/volume, with a phosphatidylcholine content of the lipid group of 30 to 99% by weight, and in which the aggregates demonstrate skin penetration dependent on the critical solubility temperature of the fluorocarbons.

6. Cosmetic preparation containing kaolin according to claim 5, characterized by the additional content of asymmetric lamellar aggregates charged solely with oxygen in the mixture.

7. Cosmetic preparation containing kaolin according to claim 5, characterized in that the aggregates, in addition to the kaolin/spherical particle mixture, contain a product of the cautious ultrasonification and/or high-pressure homogenization of suspensions or dispersions of plant cells, bacteria or yeasts.

8. Method of using a preparation containing kaolin consisting of a mixture of white kaolin with a high proportion of kaolinite and spherical inorganic particles of a particle size of less than 5 μm, with a proportion of spherical particles in the kaolin mixture of 0.5 to 10% by weight in a cosmetic mask, cosmetic gel or cosmetic cream, in which the proportion of the kaolin/spherical particle mixture lies in the range of 2.5 to 30% by weight of the total preparation.

* * * * *